United States Patent [19]
Wojtowicz

[11] 3,976,756
[45] Aug. 24, 1976

[54] PREPARATION OF HYDRAZINE AND ITS COMPOUNDS

[75] Inventor: John A. Wojtowicz, Cheshire, Conn.
[73] Assignee: Olin Corporation, New Haven, Conn.
[22] Filed: Oct. 28, 1975
[21] Appl. No.: 626,574

[52] U.S. Cl. .............................. 423/407; 423/408; 260/566 B
[51] Int. Cl.$^2$ ................. C07C 109/00; C01B 21/16
[58] Field of Search ........................ 423/407, 408; 260/566 B

[56] References Cited
UNITED STATES PATENTS

| | | | |
|---|---|---|---|
| 2,678,258 | 5/1954 | Haller | 423/408 |
| 3,382,041 | 5/1968 | Needham et al. | 423/408 |
| 3,415,882 | 12/1968 | Jenkins et al. | 260/566 B |

Primary Examiner—G. O. Peters
Attorney, Agent, or Firm—Kenneth P. Glynn

[57] ABSTRACT

A method for preparing hydrazine and its compounds is described. Hypochlorous acid in a non-aqueous solvent is reacted with a carbonyl compound and with a nitrogen-contributing compound selected from the group consisting of ammonia, primary alkyl amines and mixtures of these. Hydrazine intermediates such as azines, hydrazones, and diazacyclopropanes are obtained and these may, if desired, be converted to hydrazine and its compounds, e.g., by hydrolysis.

14 Claims, No Drawings

PREPARATION OF HYDRAZINE AND ITS COMPOUNDS

The present invention is directed to a method of making hydrazine and its compounds. More particularly, the present invention is directed to the preparation of hydrazine and its compounds by the reaction of HOCl in a non-aqueous solvent with a carbonyl compound and with a nitrogen-contributing compound selected from ammonia, primary alkyl amines and mixtures of these. Hydrazine intermediates such as azines, hydrazones and diazacyclopropanes are obtained and these may, if desired, be converted to hydrazine and its compounds, e.g., by hydrolysis.

It is well known that sodium hypochlorite may be reacted with aqueous ammonia and with a carbonyl compound to obtain hydrazine and hydrazine compounds. This method, however, has various disadvantages due to the use of sodium hypochlorite which requires large volumes of aqueous solution. Also, the sodium hypochlorite tends to convert to sodium chlorite and sodium chlorate and these are ineffective in the formation of azine and hydrazone intermediates and of hydrazine and its compounds. Further, the aqueous medium, used for both the sodium hypochlorite and for the ammonia, is difficult to separate from the final hydrazine product, and the resulting separation apparatus and operating costs have a disadvantageous effect on the economics of the process. Lastly and most significantly, this prior art process involves the costly removal of sodium chloride salt by-product from the azine and hydrazone intermediates and/or the hydrazine products.

It has now been discovered that the disadvantages of prior art methods may be overcome by the method of the present invention which involves reacting hypochlorous acid in a non-aqueous solvent with a carbonyl compound and with a nitrogen-contributing compound selected from ammonia, primary alkyl amines and mixtures of these. The azine and hydrazone compounds which are obtained may subsequently be hydrolyzed to form hydrazines and its compounds.

One of the principal reactants used in the method of the present invention is HOCl. The hypochlorous acid is used in a non-aqueous solvent solution. Among the solvents which may be used are the lower alky ketones, lower alkyl cyanides and the lower alkyl esters of lower alkanoic acids. Particularly useful are the lower alkyl ketones as solvents. These lower alkyl compounds may generally contain about 1 to about 6 carbon atoms, e.g., about 1 to about 5 carbon atoms. The solutions may contain from about 0.5 to about 50% by weight of HOCl and preferably about 5 to about 30% by weight of HOCl. Non-aqueous solvent solutions of hypochlorous acid may be obtained by known methods, e.g., as described in U.S. Pat. No. 3,718,598 issued on Feb. 27, 1973, to Wojtowicz et al, the disclosure of which is incorporated herein by reference.

The nitrogen-contributing compound used in the method of the present invention is a compound having the formula:

wherein $R_1$ is selected from hydrogen and alkyl radicals having about 1 to about 6 carbon atoms, and $R_1$ is perferably selected from hydrogen and alkyl radicals having about 1 to about 4 carbon atoms. Among the most useful compounds are ammonia and the lower alkyl primary amines such as methylamine and ethylamine. The nitrogen-contributing compound is desirably used in non-aqueous form, i.e. is advantageously employed having no more than about 10% by weight of water present, and preferably having no more than about 5% or even no more than about 0.5% by weight of water present. Thus, anhydrous ammonia is particularly useful.

The carbonyl compound which is employed as a reactant in the method of the present invention includes those having the formula:

wherein $R_2$ is selected from hydrogen and alkyl radicals having about 1 to about 6 carbon atoms and $R_3$ is selected from alkyl radicals having about 1 to about 6 carbon atoms and aryl radicals having about 6 to about 10 carbon atoms, or $R_2$ and $R_3$ together with the carbon atom shown in the formula form a cycloaliphatic ring having about 3 to about 8 carbon atoms. Preferably, $R_2$ is selected from hydrogen and alkyl radicals having about 1 to 4 carbon atoms and preferably $R_3$ is selected from alkyl radicals having about 1 to about 4 carbon atoms and a phenyl radical. Examples of suitable carbonyl compounds are acetaldehyde, propionaldehyde, methylisobutyl ketone, diethyl ketone, benzaldehyde and cyclohexanone. In the most preferable embodiments, the carbonyl compound is acetone or methyl ethyl ketone.

In the method of the present invention, generally about 1 to about 100 moles or even more of the nitrogen-contributing compound is used per mole of the hydrochlorous acid, and preferably about 25 to about 75 moles of the nitrogen-contributing compound is used. About 0.5 to about 20 moles, and preferably about 1 to about 5 moles, of carbonyl compound per mole of hypochlorous acid is used.

As mentioned above, non-aqueous solvents such as lower alkyl ketones, cyanides or esters may be used as a solvent for the HOCl in the method of the present invention. Of course, any of the non-aqueous solvents which is compatible with the reactants used in the process may be used in the method of the present invention. Regardless of the particular solvent chosen, in general, about 2 to about 100 moles of solvent and preferably about 4 to about 40 moles of solvent may be used per mole of hypochlorous acid.

The reactants and solvent used in the method of the present invention may be combined in any order, although some or all of the solvent may first be combined with the hypochlorous acid or with both the nitrogen-contributing compound and the hypochlorous acid, if desired. The reactants and solvent are combined and reacted at a temperature of about −30°C or even lower to about 100°C or higher and preferably at about −20°C to about 50°C. Advantageously, the method of the present invention may be carried out at room temperature to avoid the need for heating or cooling apparatus. As a practical matter, for a given set of reactants and solvent, the upper limit on the temperature which may be used is dictated by the reflux temperature of the lowest boiling constituent. Any pressure may be used which does not have a detrimental effect on the reactants including vacuum pressures and high positive pressures, but as a practical matter atmospheric pressure is usually employed to simplify reactor design.

The reaction products may be withdrawn from the reaction mixture in a continuous type operation so as to obtain the desired amount of product and yield. The residence time is a matter of choice, but a measurable amount of product is obtained in some cases instantaneously and generally within a few seconds. Commercially acceptable amounts of product may be obtained after a residence time of as little as about 30 seconds to about 30 minutes and preferably after a residence time of about 1 to 15 minutes. Of course, the method may be practical on a batch basis and comparable residence times are applicable.

In the method of the present invention, the product obtained by the reaction is generally a mixture of hydrazine intermediates such as azines and/or hydrazones and/or diazacyclopropanes with possibly some hydrazine and/or hydrazine compounds present. The hydrazine intermediates may be converted to the hydrazine compounds, the hydrates of these, or the salts, by well known hydrolysis techniques. Thus, the hydrazine intermediates can readily be converted to the salts of the corresponding hydrazines by treatment with an acid such as hydrochloric acid or sulfuric acid or they may be converted directly to the hydrates, for example, by distillation, under suitable pressure, or may be converted by treatment with cationic exchange resins. The present invention consequently provides for a very effective method of preparing hydrazine and its compounds as well as hydrazine intermediates.

The following examples are presented to illustrate embodiments of the present invention, but the invention is not limited thereto:

EXAMPLE 1

65 Grams of anhydrous (less than 1% water) ammonia (3.82 moles) is dissolved in 300 ml of methyl ethyl ketone (3.35 moles) being maintained at −50°C in a 3-neck 500 cc flask fitted with stirrer, thermometer, addition funnel and cold finger condenser. 50 Grams of a solution containing hypochlorous acid (176 millimoles) and 37 grams of methyl ethyl ketone (0.51 moles) and 4 grams of water is added dropwise to the other reactants in the flask. The reactants are maintained under agitation at a temperature of about −40° to −50°C by means of external cooling for a period of about 1 hour. The product, after warming to room temperature, is analyzed chromotographically. The product is found to contain di-(methyl-ethyl)-ketazine and methyl-ethyl-diazacyclopropane.

EXAMPLE 2

About 10 grams of the product mixture obtained in Example 1 is fed to a distillation apparatus including a heated flask and a condenser. About 50 grams of water is added to the product mixture and the product mixture is hydrolyzed (after acidification with $H_2SO_4$) at a temperature of about 70° to about 100°C for a period of about 30 minutes. The distilland (free of MEK), is analyzed by wet analysis (bromate-bromide) and is found to contain about 1.14 millimoles of hydrazine. Therefore, the yield of $N_2H_4$ derivatives in Example 1 was 44 millimoles.

EXAMPLE 3

Example 1 is repeated except that aqueous ammonia containing about 56% water by weight is used in place of the anhydrous ammonia. Substantial amounts of ketazine are obtained in a product mixture.

EXAMPLE 4

Example 2 is repeated except that the product mixture obtained in Example 3 is used. Substantial amounts of hydrazine are obtained.

EXAMPLE 5

A 189 gram solution containing HOCl (162.5 millimoles) and 165 grams of methyl ethyl ketone (2.30 moles) is added to a solution containing 137 grams of $CH_3NH_2$ (4.42 moles) in 300 grams of methyl ethyl ketone (4.17 moles) being maintained at about −20°C to about −10°C. The HOCl solution is added dropwise over a period of about 30 minutes while the reaction mixture is continuously stirred. The reaction product is at that time allowed to warm to room temperature and is then subjected to hydrolysis according to Example 2. The final product is analyzed and found to contain 1,2-dimethyl hydrazine (153 millimoles). The yield is determined to be about 94% based on the total HOCl employed.

What is claimed is:
1. A method of preparing azines and hydrazones which comprises, reacting:
  a. hypochlorous acid in a non-aqueous solvent;
  b. with about 1 to about 100 moles of a nitrogen-contributing compound per mole of hypochlorous acid, said nitrogen-contributing compound having the formula:

wherein $R_1$ is hydrogen or an alkyl radical having about 1 to about 6 carbon atoms; and
  c. with about 0.05 to about 20 moles of a carbonyl compound per mole of hypochlorous acid, said carbonyl compound having the formula:

wherein $R_2$ is selected from hydrogen and alkyl radicals having about 1 to about 6 carbon atoms, and $R_3$ is selected from alkyl radicals having about 1 to about 6 carbon atoms and aryl radicals having about 6 to about 10 carbon atoms, or $R_4$ and $R_5$ together with the carbon atom shown in the above formula form a cycloaliphatic ring having about 3 to about 8 carbon atoms.

2. The method of claim 1 wherein about 25 to about 75 moles of said nitrogen-contributing compound is used per mole of hypochlorous acid.

3. The method of claim 2 wherein $R_1$ is selected from hydrogen and alkyl radicals having about 1 to about 4 carbon atoms and said non-aqueous solvent is a lower alkyl ketone, cyanide or ester.

4. The method of claim 1 wherein about 1 mole to about 5 moles of said carbonyl compound is used per mole of hypochlorous acid.

5. The method of claim 4 wherein $R_2$ is selected from hydrogen and alkyl radicals having about 1 to about 4 carbon atoms and $R_3$ is selected from alkyl radicals having about 1 to about 4 carbon atoms and a phenyl radical.

6. The method of claim 5 wherein $R_1$ is selected from hydrogen and alkyl radicals having about 1 to about 4 carbon atoms.

7. The method of claim 6 wherein said carbonyl compound is acetone or methyl ethyl ketone and said non-aqueous solvent is a lower alkyl ketone.

8. A method of preparing hydrazine and its compounds which comprises:
   i. preparing azines and hydrazones by reacting:
      a. hypochlorous acid in a non-aqueous solvent;
      b. with about 1 to about 100 moles of a nitrogen-contributing compound per mole of hypochlorous acid, said nitrogen-contributing compound having the formula:

$R_1NH_2$ wherein $R_1$ is hydrogen or an alkyl radical having about 1 to 6 carbon atoms;
      c. and with about 0.5 to about 20 moles of a carbonyl compound per mole of hypochlorous acid, said carbonyl compound having the formula:

wherein $R_2$ is selected from hydrogen and alkyl radicals having about 1 to about 6 carbon atoms, and $R_3$ is selected from alkyl radicals having about 1 to about 6 carbon atoms and aryl radicals having about 6 to about 10 carbon atoms, or $R_2$ and $R_3$ together with the carbon atom shown in the above formula form a cycloaliphatic ring having about 3 to about 8 carbon atoms; and
   ii. subsequently converting said azines and hydrazones to hydrazine and its compounds by hydrolysis.

9. The method of claim 8 wherein about 25 to about 75 moles of said nitrogen-contributing compound is used per mole of hypochlorous acid.

10. The method of claim 9 wherein $R_1$ is selected from hydrogen and alkyl radicals having about 1 to about 4 carbon atoms and said non-aqueous solvent is a lower alkyl ketone, cyanide.

11. The method of claim 8 wherein about 1 mole to about 5 moles of said carbonyl compound is used per mole of hypochlorous acid.

12. The method of claim 11 wherein $R_2$ is selected from hydrogen and alkyl radicals having about 1 to about 4 carbon atoms and $R_3$ is selected from alkyl radicals having about 1 to about 4 carbon atoms and a phenyl radical.

13. The method of claim 12 wherein $R_1$ is selected from hydrogen and alkyl radicals having about 1 to about 4 carbon atoms.

14. The method of claim 13 wherein said carbonyl compound is acetone or methyl ethyl ketone and said non-aqueous solvent is a lower alkyl ketone.

* * * * *